United States Patent [19]

Suda et al.

[11] Patent Number: 5,290,698
[45] Date of Patent: Mar. 1, 1994

[54] STREPTOVERTICILLIUM FERM P-10489 WHICH PRODUCES ANTITUMOR AGENT BE-13793C

[75] Inventors: Hiroyuki Suda; Katuhisa Kojiri; Akira Okura, all of Tokyo; Kenji Kawamura, Aichi; Masanori Okanishi, Tokyo, all of Japan

[73] Assignee: Banyu Pharmaceutical Co., Ltd., Tokyo, Japan

[21] Appl. No.: 985,955

[22] Filed: Dec. 4, 1992

Related U.S. Application Data

[60] Continuation of Ser. No. 823,664, Jan. 21, 1992, Pat. No. 5,217,885, which is a division of Ser. No. 496,701, Mar. 21, 1990, Pat. No. 5,106,864.

[30] Foreign Application Priority Data

Mar. 23, 1989 [JP] Japan .................................. 1-71149

[51] Int. Cl.$^5$ ...................... C12P 17/18; C12P 17/16; C12P 17/10
[52] U.S. Cl. ................................ 435/252.1; 435/118; 435/119; 435/121; 435/127; 435/128; 435/908
[58] Field of Search ............... 435/252.1, 253.4, 253.5, 435/117, 118, 121, 128, 908

[56] References Cited

PUBLICATIONS

T. Kaneko et al., "Two Synthetic Approaches to Rebeccamycin", Tetrahedron Letters, vol. 26, No. 34, pp. 4015–4018, (1985).
J. Bergman et al., "Synthesis of Indolo[2,3-a]pyrrolo[3-,4-c]carbazoles by Double Fischer Indolizations", J. Org. Chem., vol. 54, pp. 824–828, (1989).
W. Steglich et al., "Indole Pigments from the Fruiting Bodies of the Slime Mold Arcyria Denudata", Angew. Chem. Int. Ed. Engl., vol. 19, No. 6, pp. 459–460, (1980).

Primary Examiner—David M. Naff
Assistant Examiner—L. Blaine Lankford
Attorney, Agent, or Firm—Sughrue, Mion, Zinn, Macpeak & Seas

[57] ABSTRACT

A novel antitumor substance BE-13793C or a pharmaceutically acceptable salt thereof, which is represented by the following formula:

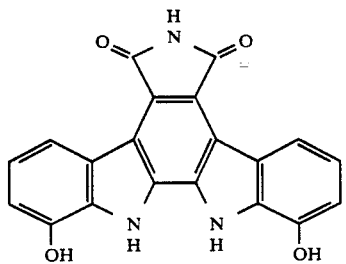

an anticancer agent comprising the novel substance or a pharmaceutically acceptable salt thereof, a method of producing the novel substance and a microorganism Streptoverticillium FERM P-10489, capable of producing the novel substance are disclosed.

1 Claim, No Drawings

5,290,698

STREPTOVERTICILLIUM FERM P-10489 WHICH PRODUCES ANTITUMOR AGENT BE-13793C

This is a continuation of application Ser. No. 07/823,664, filed Jan. 21, 1992, now U.S. Pat. No. 5,217,885, which is a divisional of application Ser. No. 07/496,701, filed Mar. 21, 1990, now U.S. Pat. No. 5,106,864.

FIELD OF THE INVENTION

The present invention relates to a novel compound which is of value in the field of medicine. More particularly, the invention relates to a novel substance which inhibits the growth and proliferation of tumor cells to produce an antitumor effect, a method of producing the novel substance, uses for the substance, and a novel microorganism belonging to the genus Streptoverticillium which produces the substance.

BACKGROUND OF THE INVENTION

In the field of cancer chemotherapy, a variety of microbial metabolites such as bleomycins or adriamycin have been used in clinical practice. However, many of these substances are not sufficiently effective for many of tumors which are clinically encountered and, moreover, the acquisition of resistance of tumor cells to these drugs, which is being made increasingly clear, has been interfering with their use in clinical cases (the Proceedings of the 47th Congress of the Japanese Cancer Association, pages 12 to 15, 1988).

Under these circumstances, there is naturally a constant demand for the development of new anticancer agents. Thus, a strong demand exists for a substance which would overcome the resistance of various types of tumors to the existing anticancer agents and be effective even in those cases which do not respond to the anticancer drugs heretofore available.

The inventors of the present invention screened a variety of microbial metabolites in search of candidate antitumor agents. As a result, it has been found that a novel compound of the following formula has an excellent antitumor activity. The present invention has been achieved on the basis of the above finding.

SUMMARY OF THE INVENTION

Accordingly, the present invention provides a novel antitumor substance, designated as BE-13793C, which is represented by the following formula:

or a pharmaceutically acceptable salt thereof. In further aspects, the present invention relates to a method of producing the antitumor substance BE-13793C, use of the substance BE-13793C as an antitumor agent, and a novel microorganism belonging to the genus Streptoverticillium which produces the substance BE-13793C.

DETAILED DESCRIPTION OF THE INVENTION

The physicochemical properties of the novel antitumor substance BE-13793C of the present invention are as follows.

Physicochemical properties of BE-13793C

Description: a yellowish orange amorphous solid or crystal.

Molecular formula: $C_{20}H_{11}N_3O_4$.

Elemental analysis: Calcd. C, 67.23%; H, 3.10%. Found C, 67.21%, H, 3.12%.

Melting point: showing no obvious decomposition point (melting point) up to 295° C.

Solubility: hardly soluble in water, soluble in methanol and highly soluble in tetrahydrofuran or dimethyl sulfoxide.

Acidity/neutrality/basicity: acidic.

Rf: 0.45 (developer: chloroform/methanol; 5:1 v/v), (Kieselgel 60 $F_{254}$, Merck).

Color reaction: Potassium permanganate: positive.

Mass spectrum (FAB-MS) (m/z): 357 $[M]^+$

Ultraviolet (UV) absorption spectrum ($\lambda_{max}^{MeOH}$, nm): 245, 298, 307, 327, 400

Infrared (IR) absorption spectrum ($\nu_{cm-1}^{KBr}$): 3430, 3270, 1743, 1710, 1590, 1485, 1408, 1335, 1290, 1245, 1060, 815, 800, 765

$^1$H-NMR (DMSO-$d_6$, δ ppm): 6.98 (2H, br d, J=7.6 Hz), 7.13 (2H, t, J=7.6 Hz), 8.42 (2H, br d, J=7.6 Hz), 10.19 (2H, br s), 10.87 (1H, br s), 11.57 (2H, br s)

$^{13}$C-NMR (DMSO-$d_6$, δ PPM) 110.9 (d), 115.2 (d), 115.5 (s), 119.7 (s), 120.6 (s) 123.0 (s), 128.7 (s), 130.0 (s), 143.3 (s), 171.2 (s)

Biological activity of BE-13793C

In vitro activity tests were performed for evaluating the inhibitory activities of the antitumor substance BE-13793C on mouse tumor cells. In the in vitro antitumor assay using P388 tumor cells, the test substance was first dissolved in dimethyl sulfoxide and the obtained solution was serially diluted with a cell culture medium containing 20% of dimethyl sulfoxide (20% v/v DMSO-RPMI-1640 medium). Then, 2 μl of the dilution was added to 200 μl of a cell culture medium (10% v/v fetal calf serum-RPMI-1640 medium) containing $2\times10^4$ or $3\times10^4$ tumor cells. Next, each mixture was incubated at 37° C. under 5% $CO_2$ for 72 hours. The viable cells were then counted with a Coulter counter. The result was compared with the control data. As a result, the antitumor substance BE-13793C showed an intense inhibitory effect on the growth of the P388 tumor cells. The concentration (IC$_{50}$) of the antitumor substance BE-13793C causing 50% inhibition on P388/S tumor cell growth was 0.7 μM, while that on P388/V cell growth was 0.7 μM.

The P388/S cells are commonly employed mouse leukemia cells while the P388/V cells are a strain of P388 leukemia cells which have acquired resistance to the anticancer agent vincristine.

Furthermore, the antitumor substance BE-13793C inhibited the growth of P388/A cells, which had acquired resistance to the anticancer agent adriamycin, and the 50% inhibitory concentration (IC$_{50}$) thereof was 1.0 μM.

The compound of the present invention called BE-13793C showed an antitumor effect on transplanted mouse Ehrlich tumor cells (ascites type). In this assay, $10^6$ (lethal dose) tumor cells per mouse were intraperitoneally administered. Then the test substance was serially diluted and intraperitoneally administered. Table 1 summarizes the results.

TABLE 1

Effect of BE-13793C on Ehrlich ascites cancer[1,2]

| Substance | Dosage, i.p.[3] (mg/kg/injection) | MST[4] (day) | MST[5,6] (% T/C) |
|---|---|---|---|
| BE-13793C | 50 | 28.6 | 218 |
|  | 20 | 26.4 | 202 |
|  | 8 | 16.0 | 122 |
| Control group | 0.25 ml | 13.1 | 100 |

(Footnotes to Table 1)
[1]Inoculum: $10^6$ Ehrlich ascites cancer cells, intraperitoneal.
[2]Host: Female ICR mice.
[3]Treatment schedule: BE-13793C was intraperitoneally administered once a day from the 1st to the 10th day.
[4]MST: Mean survival time (in days).
[5]% T/C: (Treated MST/control MST) × 100.
[6]Criteria: When % T/C ≧ 125, the test compound was considered to produce a marked antitumor effect at the particular dose.

With regard to the acute toxicity of the antitumor substance BE-13793C on female ICR mice, no death was found on the 5th day when 100 mg/kg of said substance was intraperitoneally administered once.

As described above, the antitumor substance BE-13793C of the present invention remarkably inhibits the growth of mouse cancer cells. Therefore, it is valuable as a therapeutic agent for mammalian tumors including leukemia and many tumors such as lung, stomach, colon cancers and others.

Furthermore, the present invention relates to the uses of the compound of the present invention as an anticancer drug which is in the form of a pharmaceutical composition comprising an effective amount of the compound of the present invention optionally together with inert and pharmaceutically acceptable carrier(s).

Such a pharmaceutical composition may be produced by using the compound of the present invention in combination with an inert and pharmaceutically acceptable carrier and provided in various dosage forms of oral, parenteral or topical administration. Suitable dosage forms include solid oral preparations (for example, tablet, capsule, pill, powder, granules) and liquid oral preparations (for example, solution, suspension, emulsion). Furthermore, sterile compositions which are extemporaneously reconstituted with sterile water, physiological saline or other sterile solvent for injection can also be provided. The composition may contain 10 to 100% w/w of the compound of the present invention.

The compound of the present invention may be used in the form of any salt thereof so long as it is pharmaceutically acceptable. Examples of the salt include those obtained by using inorganic or organic bases (for example, sodium hydroxide, potassium hydroxide, sodium hydrogen carbonate, triethylamine or 2-aminoethanol).

The clinically preferred dosage of the compound of the present invention depends on the specific compound to be used, type of formulating agent, frequency of administration, therapeutic target site, and characteristics of the host and of the tumor. By way of illustration, the daily dose per adult human ranges from 10 to 500 mg for oral administration and from 10 to 100 mg for parenteral, preferably intravenous, administration. Although the frequency of administration varies depending on the administration method and the patient's conditions, it is commonly sufficient to administer the compound of the present invention one to five times per day.

The method for production of BE-13793C is described hereunder. The microorganisms and mutants thereof, which are used in the production of the antitumor substance BE-13793C of the present invention, are not limited so long as they can produce the antitumor substance BE-13793C. For example, microorganism strains having the following bacteriological characteristics may be used therefor.

1. Morphology

Under a microscope, the strain shows well-developed aerial hyphae from which whirls are formed at almost constant intervals. Further, 5 to 8 secondary branches, each having 5 to 10 terminal spore chains, are observed.

Each spore is in the form of a cylinder (0.5 × 1 to 1.5 μm) and has a smooth surface.

Neither any special organ (for example, sporangium, flagella spore or sclerotium) nor fragmentation of the hyphae is observed.

2. Cultural characteristics

Table 2 shows the cultural characteristics on various agar plate media at 28° C. for 14 days.

TABLE 2

| Medium | Growth | Aerial Hypha | Color of Basal Hypha | Soluble Pigment |
|---|---|---|---|---|
| yeast-malt-agar (ISP-2) | very good flat | poor, cotton white | light brown | none |
| oatmeal-agar (ISP-3) | very good flat | poor, cotton white | yellow | none |
| starch-inorganic salt-agar (ISP-4) | very good flat | good, cotton grayish white | pale yellowish orange | none |
| glycerin-asparagine-agar (ISP-5) | very good rising | good, powder yellowish white | yellowish orange | none |
| peptone-yeast iron-agar (ISP-6) | very good wrinkled | good, powder grayish white | pale brown | none |
| tyrosine-agar (ISP-7) | very good rising | good, powder yellowish white | light brown | none |
| nutrient agar | very good flat | good, powder white | pale yellowish brown | none |
| sucrose-nitrate-agar | poor | little | colorless | none |
| glucose-asparagine-agar | poor | little | yellowish orange | none |

3. Growth temperature (yeast-malt-agar medium, 14 days)

12° C.: Poor growth and no formation of aerial hypha.
20° C.: Poor growth and no formation of aerial hypha.
28° C.: Good growth and good formation of aerial hyphae.
37° C.: Good growth but poor formation of aerial hyphae.
45° C.: No growth.

4. Physiological characteristics (1) Liquefaction of gelatin: negative. (glucose-peptone-gelatin medium)
(2) Hydrolysis of starch: positive. (starch-inorganic salt-agar medium)

(3) Coagulation and peptonization of skim milk: negative. (skim milk medium)
(4) Production of melanoid pigments: negative.
(5) Resistance to common salt: growing at a common salt content below 4% W/V. (yeast-malt-agar medium)

5. Utilization of carbon sources

The following sugars are added to a Pridham-Gottlieb agar base medium and the strain is cultured therein at 28° C. for 14 days. Table 3 shows the results.

TABLE 3

| D-glucose | + |
| D-xylose | − |
| L-arabinose | + |
| L-rhamnose | ± |
| D-fructose | + |
| D-galactose | + |
| raffinose | + |
| D-mannitol | − |
| inositol | + |
| salicin | − |
| sucrose | − |

Note:
+: available; ±: uncertain; −: unavailable.

6. Amino acid composition of cell wall

LL-diaminopimelic acid and glycine are detected.

These bacteriological characteristics suggest that the strain belongs to the genus Streptoverticillium. Reference to relevant literature inclusive of Bergey's Manual of Determinative Bacteriology 8th Edition (1974) and Hosenkin no Dotei Jikken-ho (ed. by The Society for Actinomycetes, Japan) revealed that this strain is closely relates to *Streptoverticillium mobaraense*. However, the strain differs therefrom in the utilization of raffinose and sucrose. Further, *Streptoverticillium mobaraense* shows green hyphae on an agar medium, different from the strain. These facts indicate that the strain is a novel one. Thus, it was named Streptoverticillium sp. BA-13793.

This strain was deposited Mar. 1, 1990 with the Fermentation Research Institute, Agency of Industrial Science and Technology, Ministry of International Trade and Industry, Japan under the accession number FERM P-10489, after conversion to deposition under Budapest Treaty, FERM BP-2785.

For the purposes of the present invention, all variants and mutants of the antitumor substance BE-13793C-producing microorganism may be used. Such mutants may be derived from the parent strains by the known techniques such as irradiation with X-ray or ultraviolet light, treatment with a chemical mutagen (for example, nitrogen mustard, azaserine, nitrous acid, 2-aminopurine or N-methyl-N'-nitro-N-nitrosoguanidine (NTG)), or routine transformation techniques (for example, contacting with phages, transformation, transduction or conjugation).

In order to produce the antitumor substance BE-13793C of the present invention, the BE-13793C-producing strain BA-13793 is cultured in a nutrient medium under aerobic conditions so as to give a cultured broth containing the antitumor substance BE-13793C. The nutrients to be included in the medium may be those which are commonly employed in the culture of Actinomycetes. For example, a carbon source may be selected from among commercially available glucose, glycerol, maltose, starch, sucrose, molasses, dextrin and a mixture thereof. A nitrogen source may be selected from among commercially available soybean flour, corn gluten meal, corn steep liquor, meat extract, yeast extract, cotton-seed flour, peptone, wheat germ, fish meal, inorganic ammonium salts, sodium nitrate and a mixture thereof. As inorganic salts, commercially available calcium carbonate, sodium chloride, potassium chloride, magnesium sulfate or various phosphates may be used. In addition, a trace amount of a heavy metal salt (for example, iron, cobalt, molybdenum, manganese, zinc salts) may be used, if required. Moreover, if reaming is copious, an antifoam such as various vegetable oils (for example, soybean oil or linseed oil), higher alcohols (for-example, octadecanol) and various silicone compounds may be optionally added to the medium. In addition, any other medium components (for example, boric acid salts, 3-(N-morpholino)propanesulfonic acid) may be used so long as the strain can utilize them so as to promote the production of the antitumor substance BE-13793C.

The strain can be cultured by the same procedures as those commonly used in the production of microbial metabolites Thus either solid culture or liquid culture may be employed In the case of liquid culture, either stationary culture, stirring culture, shake culture or submerged aerobic culture may be conducted, though shake culture and submerged aerobic culture under agitation are particularly preferable. The culture temperature may range from 20° to 37° C., preferably from 25° to 30° C. The PH value of the medium preferably ranges from 4 to 8. The culture may be conducted for 24 to 192 hours, preferably 48 to 120 hours.

The desired antitumor substance BE-13793C may be harvested from the cultured broth by a separation procedure commonly employed in the recovery of a microbial metabolite from a cultured broth. Since BE-13793C is contained in the culture filtrate and in the cells, it may be purified by combining conventional separation procedures employed for the recovery from a culture filtrate and cells (for example, solvent extraction, ion exchange chromatography, affinity chromatography, partition chromatography, or gel filtration). Furthermore, high performance liquid chromatography and thin layer chromatography may be used therefor.

A preferred method of separation and purification is as follows. The culture broth is first centrifuged to recover the cells, which are then extracted with an organic solvent such as methanol or acetone. The extract is concentrated under reduced pressure and the obtained concentrate in extracted with an organic solvent such as ethyl acetate. This extract is concentrated to thereby give a crude product containing BE-13793C. Next, the crude product is purified by, for example, column chromatography with Sephadex LH-20. Thus, BE-13793C can be obtained in the form of a yellowish orange crystalline substance.

The following Examples are merely intended to illustrate the invention in further detail and should by no means be construed to limit it. The present invention should be considered to encompass all modifications of the example given herein as well as all the known production, concentration, extraction and purification processes which may be applied by those skilled in the art to BE-13793C in view of the properties of BE-13793C disclosed in this specification.

EXAMPLE

Four 500 ml conical flasks each containing 100 ml of a culture medium (pH 6.7) comprising 0.1% of glucose, 2.0% of dextrin, 1.0% of corn gluten meal, 0.5% of fish meal, 0.1% of yeast extract, 0.1% of sodium chloride, 0.05% of magnesium sulfate, 0.05% of calcium chloride, 0.0002% of ferrous sulfate, 0.00004% of cupric chloride, 0.00004% of manganese chloride, 0.00004% of cobalt chloride, 0.00008% zinc sulfate, 0.00008% of sodium borate, 0.00024% of ammonium molybdate and 0.5% of 3-(N-morpholino)propanesulfonic acid were inoculated with Streptoverticillium BA-13793 strain grown on an agar slant medium. Each flask was then incubated on a rotary shaker (180 rpm) at 28° C. for 72 hours. One-milliliter aliquots of the culture were inoculated into 50 conical flasks of 500 ml capacity each containing 100 ml of the above-mentioned medium and incubated on a rotary shaker (180 rpm) at 28° C. for 120 hours. The resulting broth (about 5 l) was filtered and the cells thus obtained were washed with 500 ml of deionized water. Then, 2.5 l of methanol was added thereto and the mixture was stirred at room temperature for 1 hour. After filtering, a methanol extract was obtained. The extraction with methanol was repeated. The methanol extracts (about 5 l) were combined and concentrated to about 800 ml. The concentrate thus obtained was extracted with 3 l of ethyl acetate and the ethyl acetate extract was concentrated to dryness. The obtained residue was washed with 500 ml of chloroform. Thus, 720 mg of a crude product containing BE-13793C was obtained. This crude product was dissolved in 2 l of methanol and concentrated. The orange precipitate thus formed was filtered to thereby give 546 mg of a product containing BE-13793C. This product was dissolved in a solvent mixture (methanol/tetrahydrofuran; 1:1 v/v) and subjected to column chromatography with the use of Sephadex LH-20 (1.5×120 cm, Pharmacia) and developed with methanol/tetrahydrofuran (1:1 v/v). The BE-13793C fraction thus obtained was concentrated to thereby give 99 mg of BE-13793C in the form of a yellowish orange crystalline substance.

The antitumor substance BE-13793C of the present invention inhibits not only the growth of tumor cells showing no resistance to existing antitumor drugs but also the growth of those which have acquired the resistance against said antitumor drugs. Thus, it is highly valuable as an anticancer agent in the field of medicine.

While the invention has been described in detail and with reference to specific embodiments thereof, it will be apparent to one skilled in the art that various changes and modifications can be made therein without departing from the spirit and scope thereof.

What is claimed is:

1. A biologically pure culture of the microorganism Stetptoverticillium sp. FERM P-10489 or mutants thereof capable of producing the antitumor substance BE-13793C.

* * * * *